(12) United States Patent
Kato

(10) Patent No.: US 10,932,651 B2
(45) Date of Patent: Mar. 2, 2021

(54) OPTICAL ADAPTER FOR ENDOSCOPE AND ENDOSCOPE APPARATUS

(71) Applicant: OLYMPUS CORPORATION, Tokyo (JP)

(72) Inventor: Takahiko Kato, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 646 days.

(21) Appl. No.: 15/683,983

(22) Filed: Aug. 23, 2017

(65) Prior Publication Data

US 2018/0177384 A1 Jun. 28, 2018

(30) Foreign Application Priority Data

Dec. 27, 2016 (JP) .............................. JP2016-253903

(51) Int. Cl.
| | |
|---|---|
| *A61B 1/00* | (2006.01) |
| *A61B 1/06* | (2006.01) |
| *G02B 23/24* | (2006.01) |

(52) U.S. Cl.
CPC ...... *A61B 1/00101* (2013.01); *A61B 1/00096* (2013.01); *A61B 1/0676* (2013.01);
(Continued)

(58) Field of Classification Search
CPC ............ A61B 1/00124; A61B 1/00112; A61B 1/0071; A61B 1/0008; A61B 1/00089; A61B 1/00101; A61B 1/00103; A61B 1/00105; A61B 1/00128; A61B 1/00131; A61B 1/00135; A61B 1/00137; A61B 1/0014; A61B 1/00163; A61B 1/00174; A61B 1/002; A61B 1/04; A61B 1/042;
(Continued)

(56) References Cited

U.S. PATENT DOCUMENTS

| | | | |
|---|---|---|---|
| 2005/0177027 A1 | 8/2005 | Hirata | |
| 2005/0182291 A1* | 8/2005 | Hirata | ................ A61B 1/00096 600/101 |

(Continued)

FOREIGN PATENT DOCUMENTS

JP 2008-35884 A 2/2008

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

An adapter for an endoscope, the adapter including: a cylindrical body having an internal portion formed on the cylindrical body, the internal portion configured to matingly engage with each of distal and proximal external portions provided on a tip of the endoscope, the distal and proximal external portions being separated in a longitudinal direction of the cylindrical body by a portion of the tip that does not engage the internal portion; and wherein the cylindrical body further having an anti-slip portion formed on an exterior of the cylindrical body, the anti-slip portion having a plurality of recesses arranged circumferentially on the exterior, a position of the anti-slip portion in the longitudinal direction being set such that a position of the proximal external portion in the longitudinal direction does not overlap with the longitudinal position of the anti slip portion where the proximal external portion is engaged with the internal portion.

8 Claims, 10 Drawing Sheets

(52) U.S. Cl.
CPC ....... *G02B 23/243* (2013.01); *G02B 23/2476* (2013.01); *A61B 1/00124* (2013.01); *A61B 1/00128* (2013.01)

(58) Field of Classification Search
CPC ........... A61B 1/05; A61B 1/051; A61B 1/053; A61B 1/0676; G02B 23/243; G02B 23/2476; G02B 23/24; G02B 23/2407; G01N 21/954; G01N 2021/9544; G01N 2021/9546
USPC ........ 600/175, 109, 112, 121–122, 127, 129, 600/160, 176, 172; 356/241.1–241.6
See application file for complete search history.

(56) References Cited

U.S. PATENT DOCUMENTS

| | | |
|---|---|---|
| 2009/0234189 A1 | 9/2009 | Zen |
| 2010/0188493 A1* | 7/2010 | Kanzaki ............. A61B 1/00059 348/75 |
| 2012/0029290 A1* | 2/2012 | Nishijima ............. A61B 1/015 600/156 |
| 2013/0184531 A1 | 7/2013 | Kanzaki et al. |

* cited by examiner

OPTICAL ADAPTER FOR ENDOSCOPE AND ENDOSCOPE APPARATUS

CROSS-REFERENCE TO RELATED APPLICATION

The present application is based upon and claims the benefit of JP 2016-253903, filed on Dec. 27, 2016, the entire contents of which is incorporated herein by reference.

BACKGROUND

Field

The present application relates to an optical adapter for an endoscope detachably attached to an endoscope apparatus to be inserted into an observation object, and to an endoscope apparatus provided with the optical adapter for the endoscope.

Background

In order to cope with various observation objects, endoscope apparatuses have an insertion part which is formed into an elongated tubular shape according to the observation object, to be inserted into the inside of a tubular hollow. Among these endoscope apparatuses, known is one provided with an optical adapter for an endoscope that is detachably screwed on the tip side of the insertion part and has an optical system for observation or image pickup and an illumination optical system for illuminating the surroundings of the endoscopic object inside the tubular hollow.

The endoscope optical adapter has a connection ring (also referred to as a retaining ring/) rotatably mounted on the body part thereof so as to be screwed onto the tip of the insertion part of the endoscope apparatus. On the surface of the connection ring, for example, it is known in the prior art to provide an anti-slip portion to improve rotational handleability when the connection ring is screwed onto and screwed off the tip of the insertion part by gripping and rotating the connection ring.

Incidentally, as the demand for thinning the insertion part of the endoscope apparatus increases, the diameter of the endoscope optical adapter is also required to be reduced similarly. However, since the size of the built-in object is restricted in the optical adapter for the endoscope, it is necessary to reduce the thickness of the connection ring to be attached onto and detached from the tip of the insertion part.

However, when the diameter of the optical adapter for an endoscope is reduced, there has been a problem that the anti-slip portion of the connection ring is thinner than other portions even in a correctly attached state, which makes its strength lower than the surroundings.

Therefore, if the endoscope optical adapter is loosely attached to the tip of the insertion part, when an external force is applied to the anti-slip portion of the connection ring, the endoscope optical adapter is liable to be broken and has a possibility of falling off the tip of the insertion part.

SUMMARY

Accordingly, an adapter for use with an endoscope is provided. The adapter comprising: a cylindrical body having an internal portion formed on an interior of the cylindrical body, the internal portion being configured to matingly engage with each of distal and proximal external portions provided on an external surface of a tip of the endoscope, the distal and proximal external portions being separated in a longitudinal direction of the cylindrical body by a portion of the tip that does not engage the internal portion; and wherein the cylindrical body further having an anti-slip portion formed on an exterior of the cylindrical body, the anti-slip portion having a plurality of recesses arranged circumferentially on the exterior, a position of the anti-slip portion in the longitudinal direction being set such that a position of the proximal external portion in the longitudinal direction does not overlap with the longitudinal position of the anti slip portion in a state where the proximal external portion is engaged with the internal portion of the cylindrical body.

The internal portion can be an internal threaded portion and the distal and proximal external portions can be distal and proximal threaded portions each being configured to matingly engage with the internal threaded portion.

In the state where the proximal external portion is engaged with the internal portion, at least a portion of the distal external portion can overlap with the anti-slip portion in the longitudinal direction.

The anti-slip portion can be formed on the cylindrical body at a portion of the cylindrical body having a first wall thickness, a second wall thickness is greater than the first wall thickness, the anti-slip portion being positioned in the longitudinal direction so that the distal external portion is not located at a boundary between the portion having the first wall thickness and a portion having the second wall thickness, in a state where the internal portion is not engaged with the proximal external portion and the cylindrical body is prevented from falling off the tip by the distal external portion.

The anti-slip portion can be positioned so as to overlap with at least a part of the distal external portion in the longitudinal direction in the state where the proximal external portion is engaged with the internal portion.

Each of the plurality of recesses can have a side surface having an angle of 90° or less with respect to a surface of the outer periphery of the connection ring.

The adapter can further comprise one or more optical elements arranged on the cylindrical body.

Also provided is an endoscope apparatus comprising: the tip; and the adapter for an endoscope.

Still further provided is an adapter for an endoscope, where the adapter comprising: a cylindrical body having distal and proximal internal portions provided on an internal surface of the cylindrical body, each of the distal and proximal internal portions being configured to matingly engage with an external portion on an external surface of a tip of the endoscope, each of the distal and proximal internal portions being separated in a longitudinal direction of the cylindrical body by a portion of the cylindrical body that does not engage the external portion; and wherein the cylindrical body further having an anti-slip portion formed on an exterior of the cylindrical body, the anti-slip portion having a plurality of recesses arranged circumferentially on the exterior, a position of the anti-slip portion in the longitudinal direction being set such that a position of the proximal internal portion in the longitudinal direction does not overlap with the longitudinal position of the anti-slip portion in a state where the distal internal portion is engaged with the external portion.

The distal and proximal internal portions can be distal and proximal internal threaded portions and the external portion can be an external threaded portion, the distal and proximal internal threaded portions each being configured to matingly engage with the external threaded portion.

In the state where the distal internal portion is engaged with the external portion, at least a portion of the proximal internal portion does not have to overlap with the anti-slip portion in the longitudinal direction.

The anti-slip processed portion can be formed at the longitudinal position of the cylindrical body so that the external portion is not located at a boundary between a portion of the cylindrical body having a first wall thickness and a portion of the cylindrical body having a second wall thickness, where the second wall thickness is greater than the first wall thickness, in a state where the distal internal portion is disengaged with the external portion and the cylindrical body is prevented from falling off the tip by the proximal internal portion.

The distal internal portion and the proximal internal portion can be provided at a predetermined distance from each other in a longitudinal direction of the connection ring.

Each of the plurality of recesses can have a side surface having an angle of 90° or less with respect to a surface of the outer periphery of the connection ring.

The adapter can further comprise one or more optical elements arranged on the cylindrical body.

Still further yet provided is an endoscope apparatus comprising: the tip; and the adapter for an endoscope.

DETAILED DESCRIPTION

Figure 1:
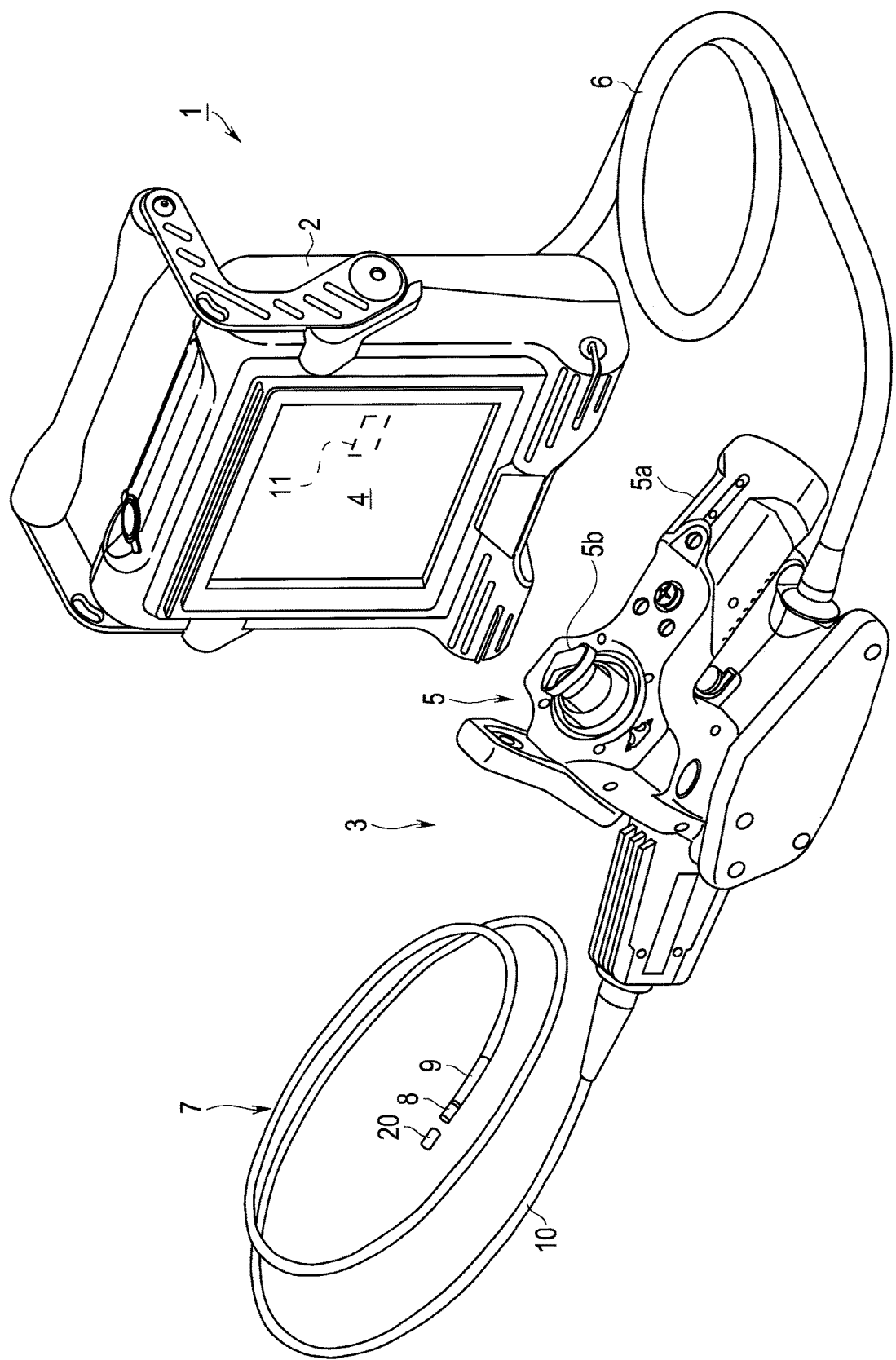
FIG. 1 is a perspective view showing a configuration of an endoscope apparatus and an optical adapter for an endoscope.

Embodiments will be described below with reference to the drawings. In each drawing used in the following description, in order to make each component to be recognizable on the drawing, the scales of respective components are made different, and the embodiments are not limited only to the number of components, the shapes of the components, the ratio of sizes of the components, and the relative positional relationship of the components described in these drawings. In addition, in the following description, there are cases where description is made by expressing the up-down direction as viewed toward the paper surface of the drawing as an upper part and lower part of a component.

First, an endoscope apparatus will be described below. In addition, an optical unit and an endoscope will be described below with reference to the drawings.

Figure 2:
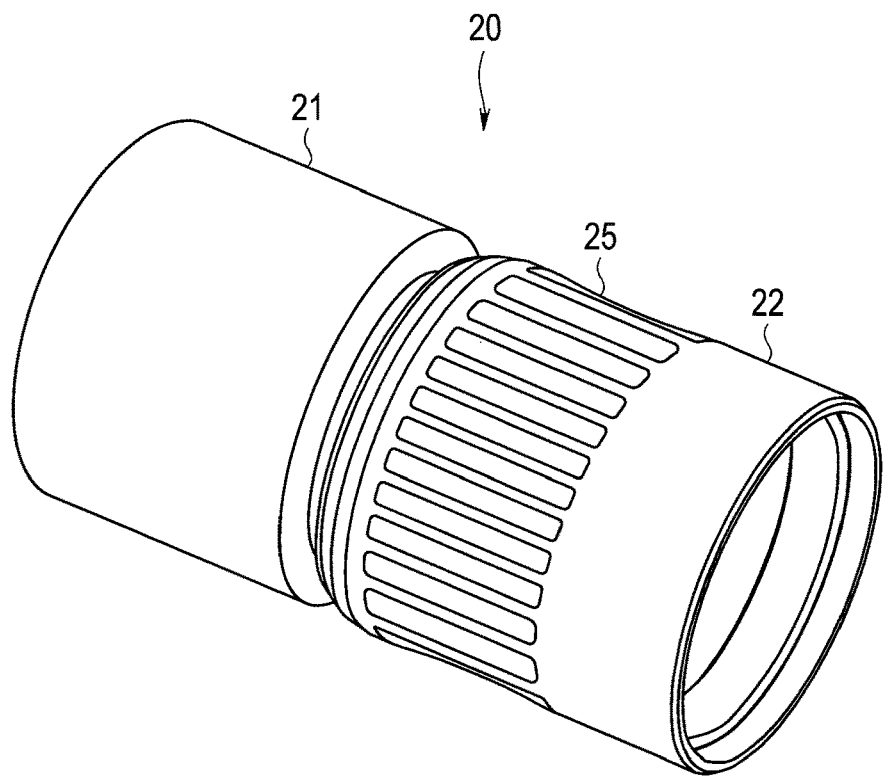
FIG. 2 is a perspective view showing a configuration of the optical adapter.
Figure 3:
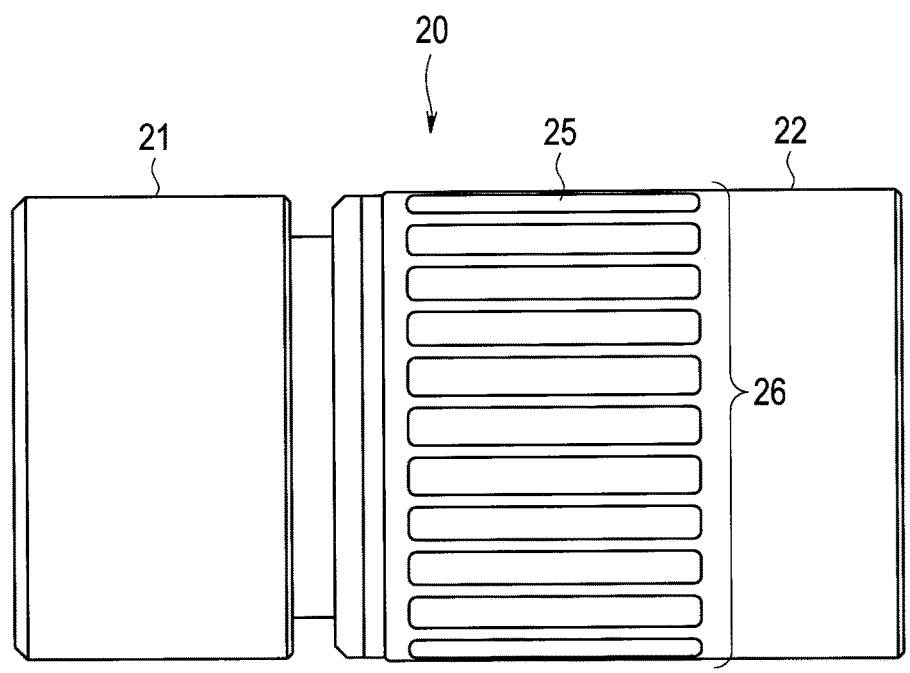
FIG. 3 is a side view showing the configuration of the optical adapter.
Figure 4:
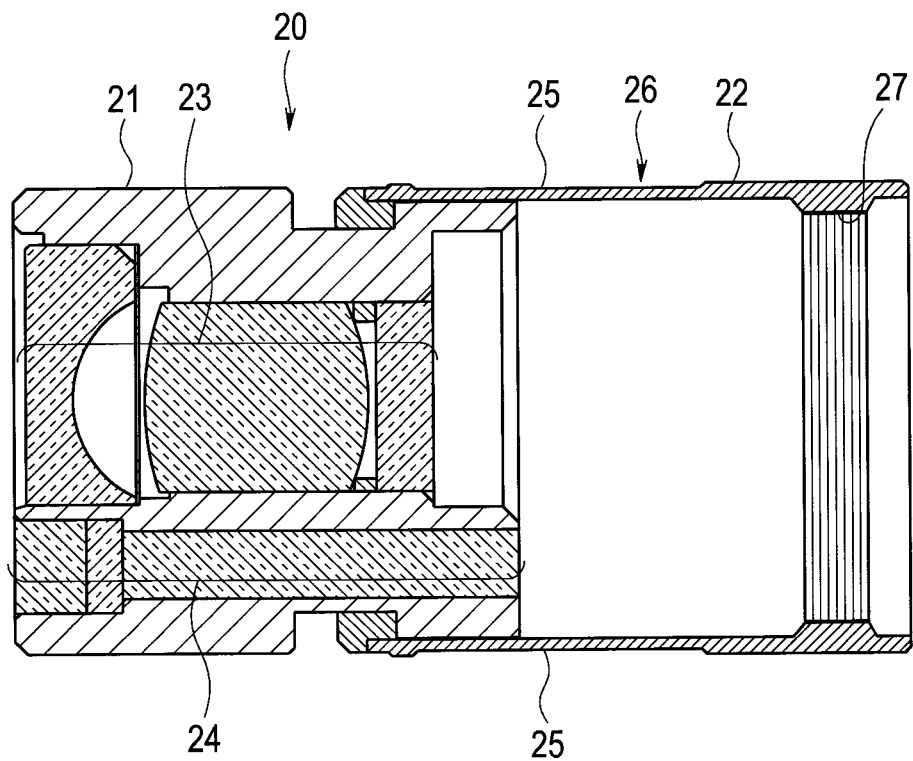
FIG. 4 is a cross-sectional view showing the configuration of the optical adapter.
Figure 5:
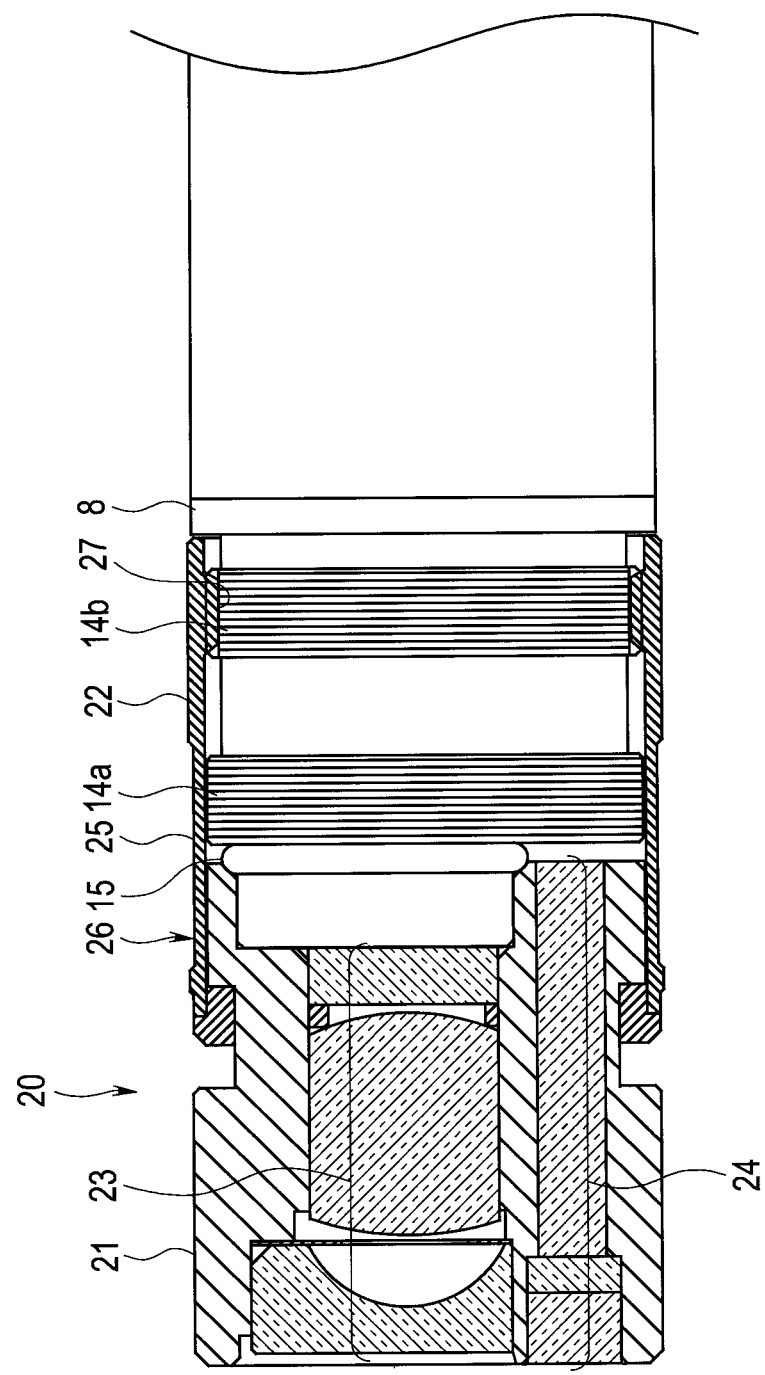
FIG. 5 is a partial cross-sectional view showing a state in which the optical adapter is attached to a tip of the endoscope.
Figure 6:
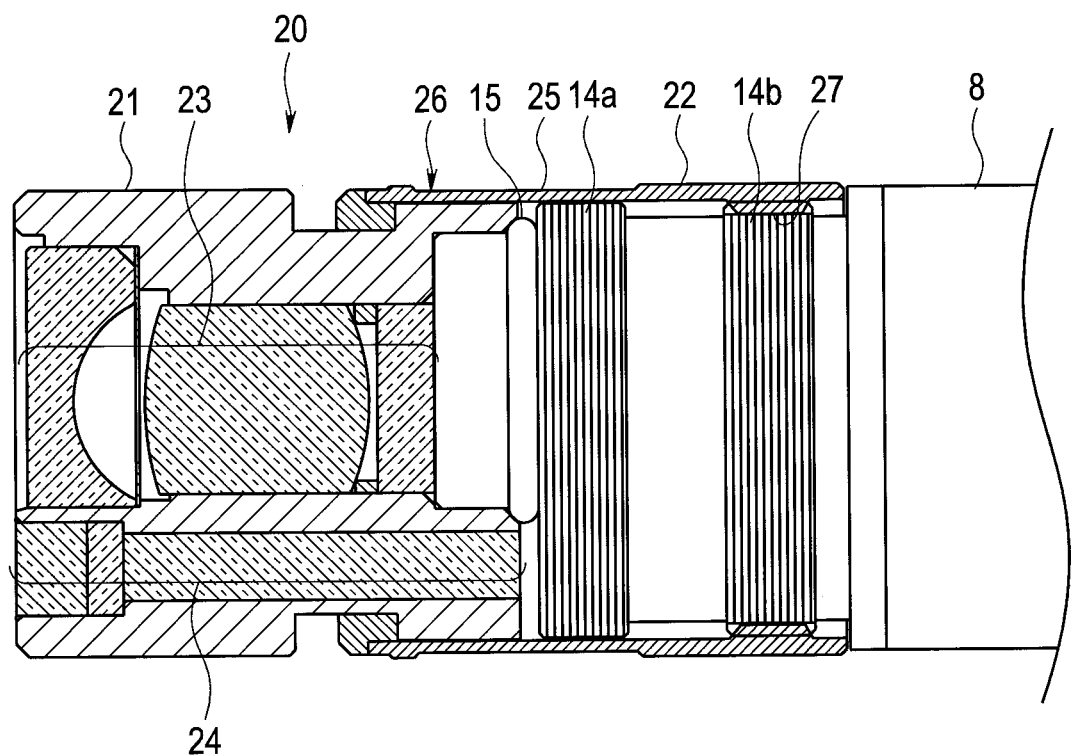
FIG. 6 is a partial cross-sectional view showing a state in which the optical adapter is correctly attached to the tip of the endoscope.
Figure 7:
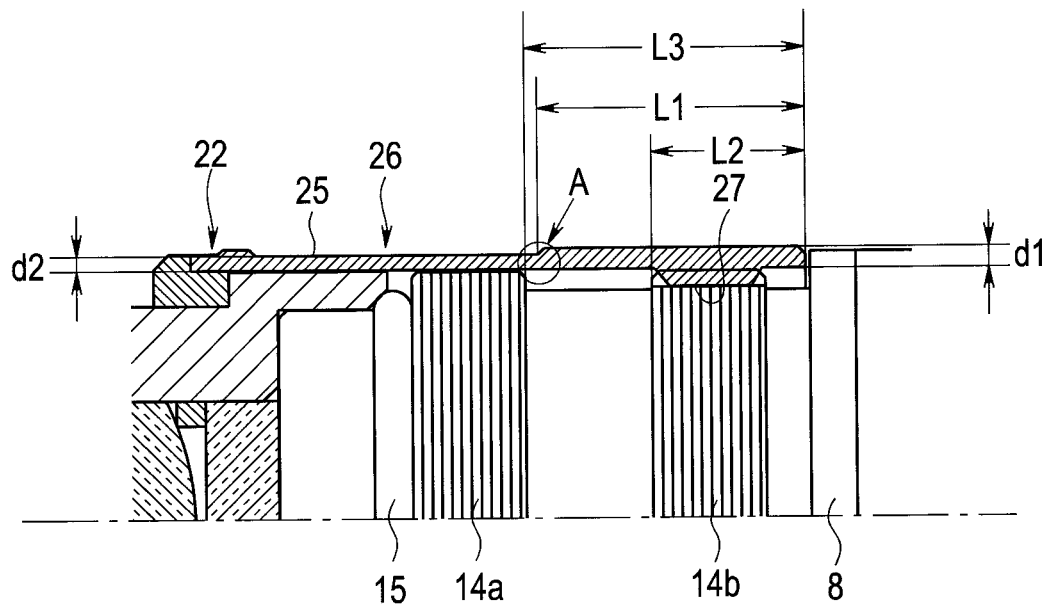
FIG. 7 is a partially enlarged cross-sectional view showing the state in which the optical adapter is correctly attached to the tip of the endoscope.
Figure 8:
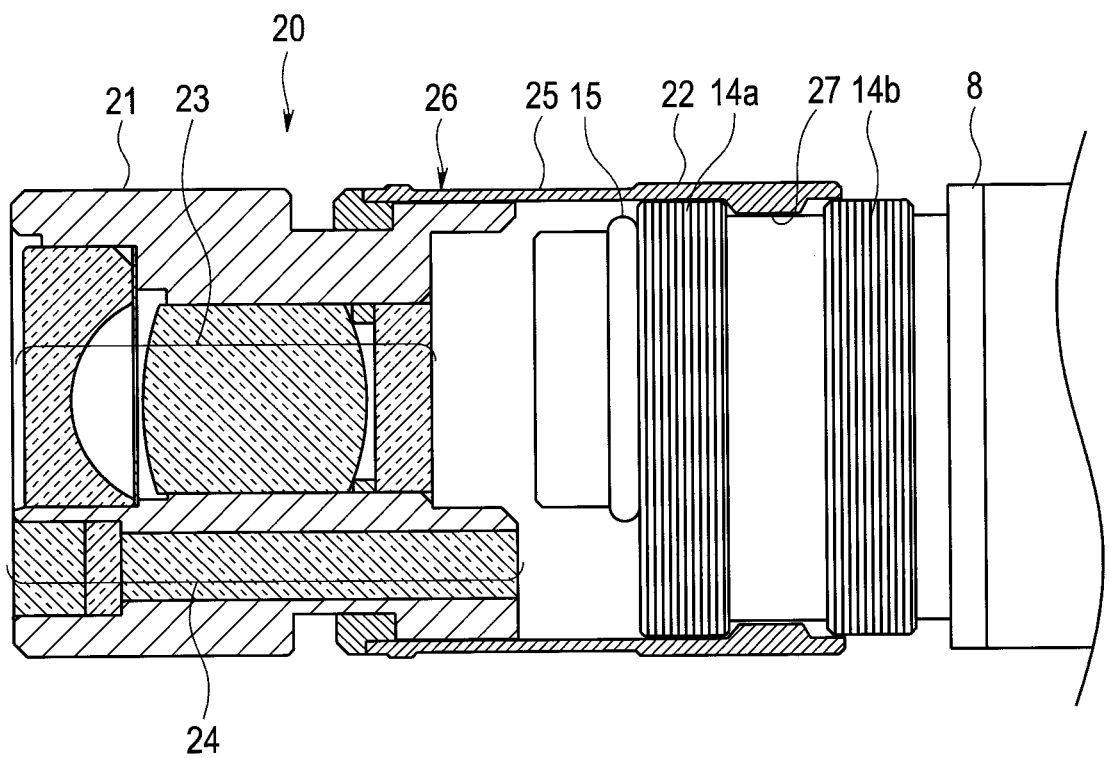
FIG. 8 is a partial cross-sectional view showing a state in which the optical adapter is incorrectly attached to the tip of the endoscope.
Figure 9:
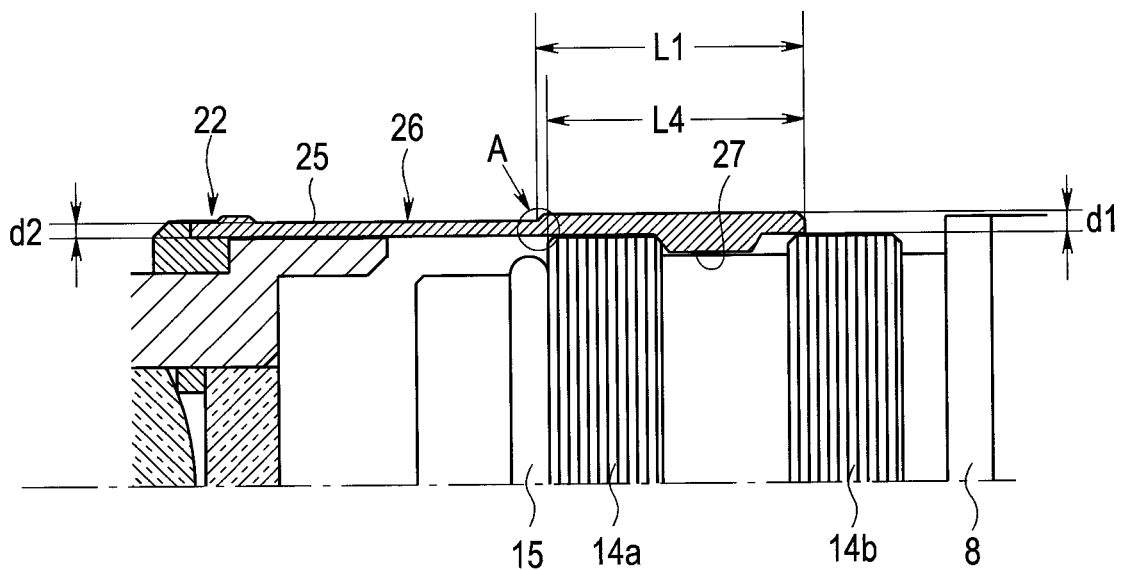
FIG. 9 is a partially enlarged cross-sectional view showing the state in which the optical adapter is incorrectly attached to the tip of the endoscope.

FIG. 1 is a perspective view showing a configuration of an endoscope apparatus and an optical adapter for an endoscope, FIG. 2 is a perspective view showing a configuration of the optical adapter, FIG. 3 is a side view showing the configuration of the optical adapter, FIG. 4 is a cross-sectional view showing the configuration of the optical adapter, FIG. 5 is a partial cross-sectional view showing a state in which the optical adapter is attached to a tip of the endoscope, FIG. 6 is a partial cross-sectional view showing a state in which the optical adapter is correctly attached to the tip of the endoscope, FIG. 7 is a partially enlarged cross-sectional view showing the state in which the optical adapter is correctly attached to the tip of the endoscope, FIG. 8 is a partial cross-sectional view showing a state in which the optical adapter is incorrectly attached to the tip of the endoscope, and FIG. 9 is a partially enlarged cross-sectional view showing the state in which the optical adapter is incorrectly attached to the tip of the endoscope.

Hereinafter, a schematic configuration of the endoscope apparatus including the optical adapter of the present embodiment will be described.

As shown in FIG. 1, the endoscope apparatus 1 of the present embodiment has a configuration in which an optical adapter 20 is attachable and detachable.

First, the configuration of the endoscope 1 will be described below.

As shown in FIG. 1, the endoscope apparatus 1 is configured to include an apparatus body 2 as a main unit and a scope unit 3 as an endoscope connected to the apparatus body 2.

The apparatus body 2 has a liquid crystal panel (hereinafter referred to as an LCD for short) 4 as a display device on which endoscope images, operation menus and the like are displayed. The LCD 4 is a display unit for displaying an endoscopic image. A touch panel may be provided on the LCD 4.

The scope unit 3 includes an operating section 5 as an endoscope operating section, a universal cable 6 connecting the operating section 5 and the apparatus body 2, and an endoscope insertion part 7 composed of a flexible insertion tube. Incidentally, the operating section 5 and the apparatus body 2 are endoscope casings in the endoscope apparatus 1.

The endoscope insertion part 7 is inserted into objects, such as the inside of an engine, which is an observation object. The endoscope insertion part 7 includes, in order of position from the tip side, a tip 8 incorporating an image pickup optical system and an illumination optical system (which are not shown), a bendable bending portion 9, and an elongated flexible tube 10 having flexibility, which are connected in series.

Here, an industrial endoscope in which an inspection object into which the endoscope insertion part 7 is inserted is a structure, such as a machine, a building, or the like is shown as an example of the endoscope apparatus 1, but also the endoscope 1 includes a configuration applicable to a medical endoscope for observing the inside of an organism such as a human body. Furthermore, the endoscope apparatus 1 may be configured as a so-called rigid endoscope that does not have the deformable flexible tube 10 in the endoscope insertion part 7.

The scope unit 3 is attachable to and detachable from the apparatus body 2 via the universal cable 6. An image pickup unit (not shown) is built in the tip 8 of the endos cope insertion part 7. The image pickup unit is composed of an image pickup sensor such as a CCD sensor or a CMOS sensor and an image pickup optical system such as a lens disposed on the image pickup surface side of the image pickup sensor.

Further, an image pickup section (not shown) having an objective optical system is built in the tip 8, and an illumination window (not shown) constituting the illumination optical system is provided on the tip 8, and then a light-guide-fiber light emitting end is opposed to the illumination window (none of which are shown).

The tip 8 is configured so that an endos cope optical adapter (alternatively referred to as an optical adapter) 20 can be detachably attached thereto. A detailed description of the optical adapter 20 will be given later.

The bending portion 9 is provided on the proximal end side of the tip 8. The bending portion 9 is configured by connecting joint pieces (not shown) in series to be able to bend in predetermined directions. In the present embodiment, the bending portion 9 is configured to be bendable in four directions, up, down, right and left.

The operating section 5 includes a grip 5a which is a gripping portion and a bending lever 5b of a joystick type, and various operation buttons such as a freeze button and a recording instruction button are provided on the grip 5a. The user can perform image pickup, moving image recording, still image recording of an object, and the like by operating the various operation buttons.

Further, the user can bend the bending portion 9 in a desired direction by operating the bending lever 5b in the upward, downward, leftward, and rightward (U/D/L/R) directions.

Furthermore, in the case of the configuration in which the touch panel is provided on the LCD 4, the user can also make instruction about various operations of the endoscope apparatus 1 by operating the touch panel.

The apparatus body 2 is connected to the operating section 5 via the universal cable 6. Inside the universal cable 6, a signal line connected to an image pickup element, an electric wire for supplying power to the element unit, and the like are inserted (none of which are shown).

The apparatus body 2 is provided with a camera controller for performing signal processing on the image pickup element provided in the tip 8, a recording devicefor recording the processed image, and the like, and further batteries for supplying power to the camera controller, the recording device, and the like are also provided (none of which are shown).

The image data of the endoscopic image obtained by capturing an image is inspection data of an inspection object and is recorded in a memory card 11 which is a recording medium of the recording device. The memory card 11 is attachable to and detachable from the apparatus body 2. Incidentally, although being recorded on the memory card 11, the image data may be recorded in a memory (not shown) built in the apparatus body 2.

Next, the configuration of the optical adapter 20 of the endoscope apparatus 1 will be described below.

As shown in FIGS. 2 and 3, the optical adapter 20 includes a substantially cylindrical lens holding frame 21 provided on a distal end side, and a retaining ring 22 which is an annular connection ring rotatably fitted around the proximal end portion of the lens holding frame 21.

As shown in FIG. 3, recesses 25 each having a rectangular shape in a cross section are formed to extend in the longitudinal direction on the outer periphery of the retaining ring 22, and a plurality of these recesses 25 are arranged side by side in the circumferential direction. That is, a plurality of recesses 25 formed in the outer periphery of the retaining ring 22 are arranged to constitute a grooved portion 26 as a anti-slip processed portion processed so that its cross section orthogonal to the longitudinal direction has irregularities. In this disclosure, the terms "recess" and "irregularities" are used to mean any surface indentation, including grooves and knurls, for facilitating grasping of a surface by a user.

As shown in FIG. 4, an objective optical system 23 composed of a plurality of objective lens groups and an illumination optical system 24 including an illumination lens and a light guide for transmitting illumination light are incorporated in the lens holding frame 21. A threaded portion 27 is formed on the inner periphery of the retaining ring 22.

The optical adapter 20 is removably attached by screwing the retaining ring 22 onto the tip 8 of the insertion part 7 of the endoscope apparatus 1, and thereby the optical characteristics of the endoscope apparatus 1 can be changed.

To be specific, as shown in FIG. 5, the tip 8 of the endoscope insertion part 7 is inserted through the opening of the retaining ring 22, and the threaded portion 27 which is the female threaded portion of the retaining ring 22, passes through a tip-side first threaded portion 14a which is the male threaded portion for falling prevention, which is the front side of a two-step threaded portion formed on the outer periphery of the tip 8, and then the threaded portion 27 is screwed onto a tip-side second threaded portion 14b which is a male threaded portion as a portion to be used for mounting and fixing, located on the rear side in the insertion direction of the endoscope insertion part 7, namely, the rear side when the distal end surface of the tip 8 is the front side, whereby the optical adapter 20 is attached to the tip 8 of the endoscope 1 in a correctly attached state. It should be noted that the tip-side first threaded portion 14a and the tip-side second threaded portion 14b are at a predetermined distance away from each other.

At this time, the optical adapter 20 is attached to the tip 8 watertightly in a state in which an O-ring 15 provided at the tip 8 is in close contact with the proximal end surface of the lens holding frame 21 of the optical adapter 20.

It should be noted that there are a plurality of types of the optical adapter 20, and thereby it is possible to change various optical characteristics such as the view angle including close-up photographing, a wide angle, enlargement (telephoto), and the observation direction including direct viewing, side viewing, and oblique viewing, according to the type of the optical adapter attached to the tip 8 of the endoscope apparatus 1.

Here, the configuration of the grooved portion 26 formed on the outer periphery of the retaining ring 22 of the optical adapter 20 will be described below.

First, a state will be described in which the optical adapter 20 is correctly attached to the tip 8 of the endoscope 1, that is, as shown in FIGS. 6 and 7, the threaded portion 27 of the retaining ring 22 has been screwed onto the tip-side second threaded portion 14b which is the rear side of the two-step threaded portion provided on the tip 8.

In this state, the retaining ring 22 of the optical adapter 20 is configured so that the threaded portion 27 is threadedly engaged with the tip-side second threaded portion 14b so as to allow the plurality of recesses 25 constituting the grooved portion 26 made by irregularity formation to cover the tip-side first threaded portion 14a which is the front side of the two-step threaded portion.

That is, in a state in which the threaded portion 27 has been screwed onto the tip-side second threaded portion 14b and the optical adapter 20 is correctly attached to the tip 8, the retaining ring 22 has a thin portion having a thickness d2 thinner than a thickness d1 in other portions of the retaining ring 22, as shown in FIG. 7. Such thin portion is due to formation of the plurality of recesses 25, and the thin portion does not overlap with the tip-side second threaded portion 14b and is formed so as to cover the tip-side first threaded portion 14a.

Therefore, the plurality of recesses 25 of the retaining ring 22 are formed on the outer periphery toward the front side from the position at a predetermined distance L1 from the proximal end of the retaining ring 22. The threaded portion 27 of the retaining ring 22 is formed on the inner periphery on the rear side of the position at a predetermined distance L2 from the proximal end of the retaining ring 22 which are threadedly engaged with the tip-side second threaded portion 14b located on the rear side of the tip 8 so that the optical adapter 20 is correctly mounted on the tip 8 of the endoscope 1.

Further, in a state in which the optical adapter 20 is correctly attached to the tip 8, the tip-side first threaded portion 14a, which is on the front side of the tip 8 is formed on the outer periphery of the tip 8 toward the front side from the position at a predetermined distance L3 from the proximal end of the retaining ring 22.

That is, in a state in which the optical adapter 20 is correctly attached to the tip 8, the tip-side first threaded portion 14a is provided so that the proximal end thereof is located at the predetermined distance L3 from the proximal end of the retaining ring 22.

It should be noted that, in a state in which the optical adapter 20 is correctly mounted on the tip 8, it is sufficient if the tip-side first threaded portion 14a is formed so that a part of the tip-side first threaded portion 14a overlaps with (is superposed on) a portion having the thickness d2, which is the thinnest portion where the plurality of recesses 25 of the retaining ring 22 are formed.

With such a configuration, in a state in which the optical adapter 20 is correctly attached to the tip 8, the thin portion where the grooved portion 26 of the retaining ring 22 is formed covers the tip-side first threaded portion 14a of the tip 8, and thus even when external force such as force in a lateral direction is applied, since the tip 8 is fitted into the retaining ring 22, breakage hardly occurs at a boundary A where the wall thickness changes from the thickness d1 on the proximal end side of the grooved portion 26 into the thickness d2.

Next, the state will be described, in which the optical adapter 20 is incorrectly attached to the tip 8 of the endoscope 1, and falling of the optical adapter 20 is suppressed due to the contact of the threaded portion 27 of the retaining ring 22 with the tip-side first threaded portion 14a of the tip 8, that is, as shown in FIGS. 8 and 9, the state where the threaded portion 27 of the retaining ring 22 is disengaged from the tip-side second threaded portion 14b which is the rear side of the two-step threaded portion provided at the tip 8 will be described.

In this state, as shown in FIG. 9, the retaining ring 22 of the optical adapter 20 is configured such that the thick portion having the original thickness d1 covers the tip-side first threaded portion 14a.

Accordingly, in a state where the optical adapter 20 is incorrectly attached to the tip 8, the tip-side first threaded portion 14a, which is on the front side of the tip 8, is formed on the outer periphery of the tip 8 toward the rear side from the position at a predetermined distance L4 from the proximal end of the retaining ring 22.

That is, in a state where the optical adapter 20 is incorrectly attached to the tip 8, the tip-side first threaded portion 14a is provided such that the distal end thereof is located at the predetermined distance L4 from the proximal end of the retaining ring 22.

In other words, the tip-side first threaded portion 14a is formed on the tip 8 so that the predetermined distance L4 to the position where the distal end of the tip-side first threaded portion 14a is located from the proximal end of the retaining ring 22 is shorter than the predetermined distance L1 to the position where the plurality of recesses 25 constituting the grooved portion 26 are formed from the proximal end of the retaining ring 22 (L4<L1).

With such a configuration, in a state where the optical adapter 20 is incorrectly attached to the tip 8, since a portion having the original thickness d1 of the retaining ring 22 is located on the proximal end side while covering the tip-side first threaded portion 14a of the tip 8, a load can be prevented from being applied most to the boundary A where the wall thickness changes from the thickness d1 of the proximal end side of the plurality of recesses 25 constituting the grooved portion 26 into the thickness d2 when the external force such as the lateral direction is applied.

That is, in the conventional configuration, when an external force is applied to the optical adapter 20 in a state where the threaded portion 27 of the retaining ring 22 is detached from the tip-side second threaded portion 14b of the two-step threaded portion, the retaining ring 22 will be broken at the contact portion when the tip-side first threaded portion 14a of the two-step threaded portion is in contact with the inner wall surface (inner circumferential surface) of the retaining ring 22 and this contact portion is in the grooved portion 26 having a small thickness.

Since the boundary between a portion having the thickness d2 of the plurality of recesses 25 constituting the grooved portion 26 and a portion having the original thickness d1 of the retaining ring 22 is a part that can be most easily broken (boundary A) when an external force is applied to the optical adapter 20, the endoscope apparatus 1 and the optical adapter 20 have configurations to prevent the retaining ring 22 from being broken, by determining the position for forming the tip-side first threaded portion 14a and the tip-side second threaded portion 14b as the two-step threaded portion formed on the tip 8 and the grooved portion 26 of the retaining ring 22 so that the maximum load does not occur at the boundary A.

As described above, in the endoscope apparatus 1, even in the configuration in which the diameter of the insertion part 7 is reduced and the diameter of the optical adapter 20 is similarly reduced, and even if external force is applied to the optical adapter 20 attached to the tip 8 when the optical adapter 20 is loosened, the retaining ring 22 which is a connection ring of the optical adapter 20 is prevented from breaking and prevents the optical adapter 20 from falling off the tip 8.

Accordingly, configurations of the optical adapter 20 and the endoscope apparatus 1 are provided in which the diameters of the insertion part 7 and the optical adapter 20 can be reduced, and the attachment portion for mounting on the tip 8 of the insertion part 7 is prevented from being broken and is prevented from falling off the tip 8.

First Modification Example

Figure 10:
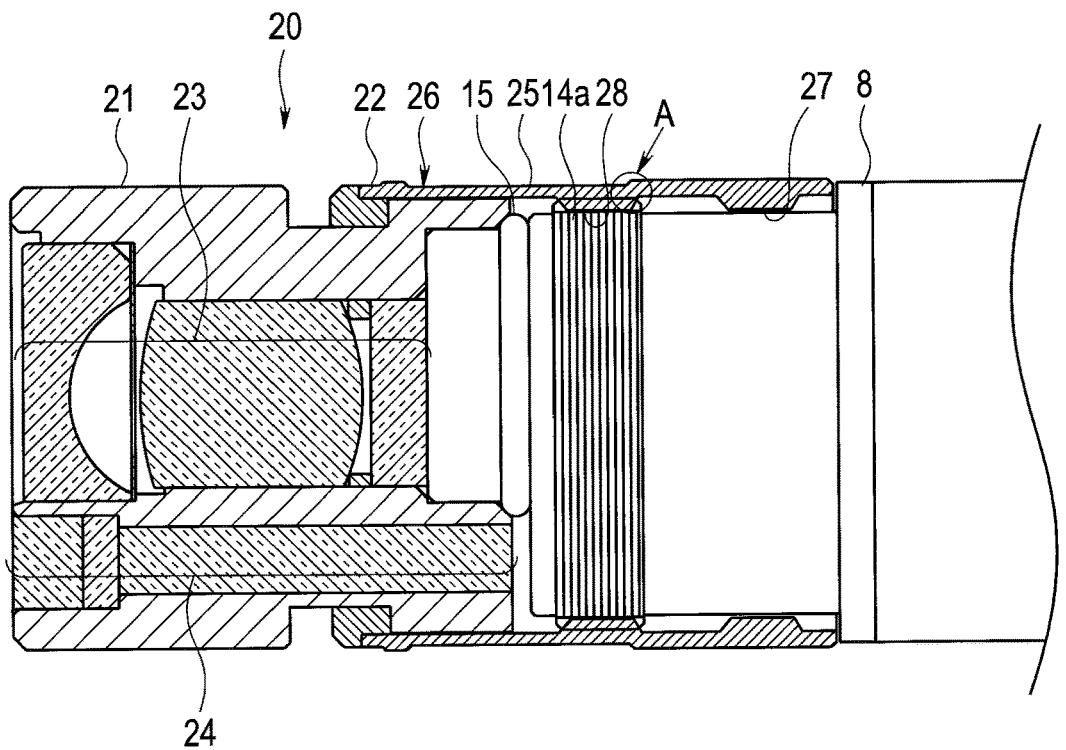
FIG. 10 is a cross-sectional view showing a configuration of the optical adapter attached to the tip of the endoscope of a first modification example.
Figure 11:
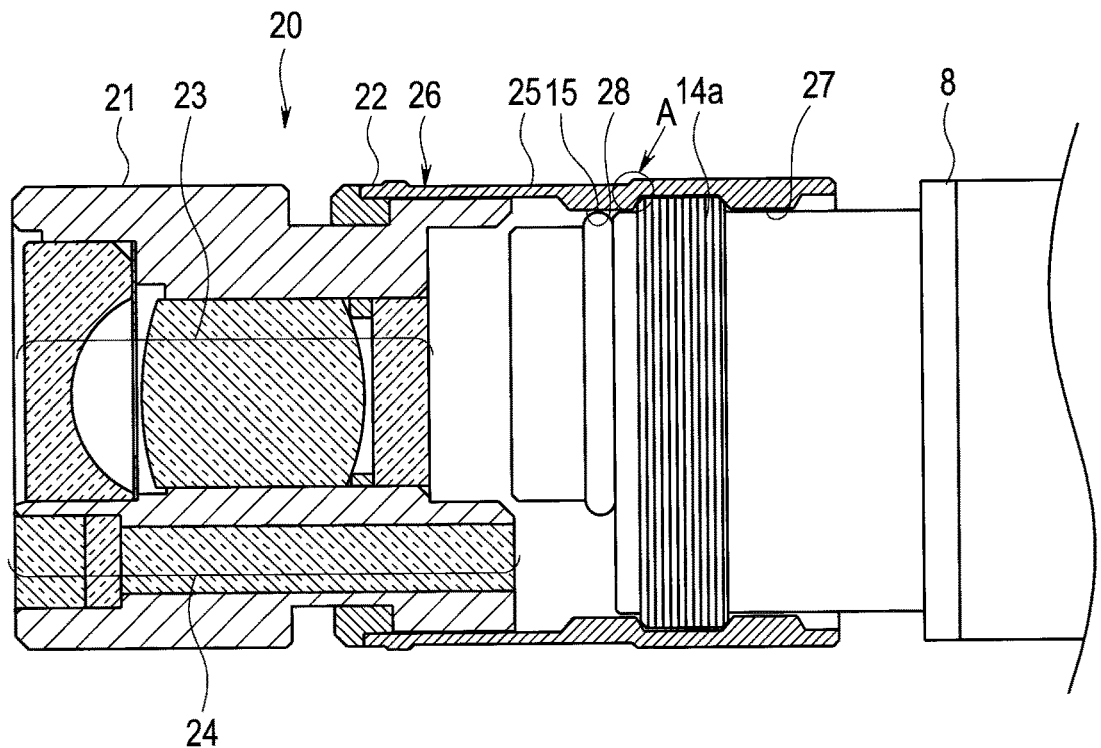
FIG. 11 is a partially enlarged cross-sectional view showing a state in which the optical adapter of the first modification example is incorrectly attached to the tip of the endoscope.
Figure 12:
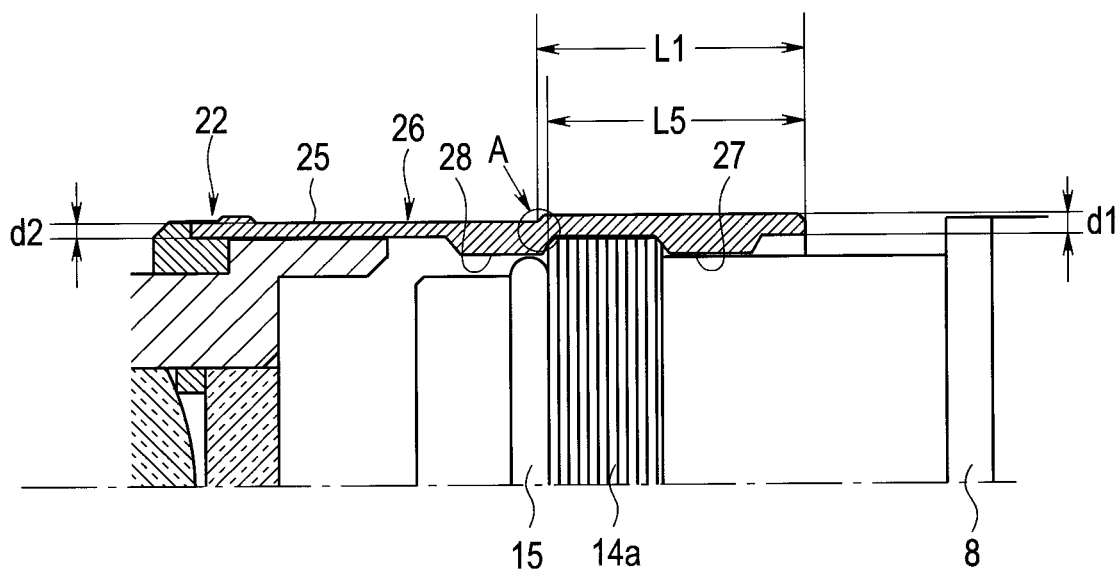
FIG. 12 is a partially enlarged cross-sectional view showing the state in which the optical adapter of the first modification example is incorrectly attached to the tip of the endoscope.

FIG. 10 is a cross-sectional view showing a configuration of the optical adapter attached to the tip of the endoscope of a first modification example. FIG. 11 is a partially enlarged cross-sectional view showing a state where the optical adapter of the first modification example is incorrectly attached to the tip of the endoscope. FIG. 12 is a partially enlarged cross-sectional view showing the state where the optical adapter of the first modification example is incorrectly attached to the tip of the endoscope.

As shown in FIG. 10, a two-part threaded portion may be employed, which is provided with an adapter-side first threaded portion 28 for mounting and fixing, located on the front side of the inner periphery of the retaining ring 22 at a predetermined distance from the adapter-side second threaded portion 27, in addition to the threaded portion 27 described above, by using the threaded portion 27 as an adapter-side second threaded portion for preventing falling.

It should be noted that the tip 8 here does not have the two-step threaded portion, and only the tip-side first threaded portion 14a is provided. As shown in FIG. 10, in a state where the optical adapter 20 is correctly attached to the tip 8 of the endoscope 1, the adapter-side first threaded portion 28 of the retaining ring 22 has been screwed onto the tip-side first threaded portion 14a of the tip 8.

As shown in FIG. 11, in a state where the optical adapter 20 is incorrectly attached to the tip 8 of the endoscope 1, the adapter-side second threaded portion 27 provided on the rear side of the retaining ring 22 comes in contact with the tip-side first threaded portion 14a of the tip 8 to prevent the optical adapter 20 from falling.

The optical adapter 20 of the present modification example has a configuration for preventing breakage of the retaining ring 22 when an external force is applied to the optical adapter 20, by providing the adapter-side first threaded portion 28 such that the boundary between a portion having the thickness d2 of the plurality of recesses 25 constituting the grooved portion 26 and a portion having the original thickness d1 of the retaining ring 22 overlaps with the most breakable portion (boundary A) so that the positions where the adapter-side first threaded portion 28 and the grooved portion 26 of the retaining ring 22 are formed are determined in order to improve the rigidity.

To be specific, as an example thereof, in a state where the optical adapter 20 is incorrectly attached to the tip 8, the adapter-side first threaded portion 28 to be formed on the retaining ring 22 is formed toward the distal end side from a position on the inner periphery, which is at a predetermined distance L5 from the proximal end of the retaining ring 22 and has the original thickness d1, as the proximal end of the retaining ring 22.

Then, a plurality of recesses 25 constituting the grooved portion 26 are formed on the retaining ring 22 so that the predetermined distance L1 of the plurality of recesses 25 constituting the grooved portion 26 from the proximal end of the retaining ring 22 is longer than the predetermined distance L5 (L5<L1) with respect to the proximal end position of the adapter-side first threaded portion 28, which is at the predetermined distance L5 from the proximal end of the retaining ring 22.

That is, the adapter-side first threaded portion 28 is provided so as to extend over the boundary A where the wall thickness changes from the thickness d1 of the proximal end side of the plurality of recesses 25 constituting the grooved portion 26 into the thickness d2.

With such a configuration, in a state where the optical adapter 20 is incorrectly attached to the tip 8, since the adapter-side first threaded portion 28 is provided at the boundary A where the wall thickness changes from the thickness d1 of the proximal end side of the plurality of recesses 25 constituting the grooved portion 26 into the thickness d2, when the external force such as the lateral direction is added, breakage can be prevented by improving the rigidity even if a load is applied there.

With such a configuration, even if an external force is applied when the optical adapter 20 attached to the tip 8 has been loosened, the retaining ring 22 which is a connection ring of the optical adapter 20 is hardly broken, and the optical adapter 20 can be prevented from falling off the tip 8.

Second Modification Example

Figure 13:
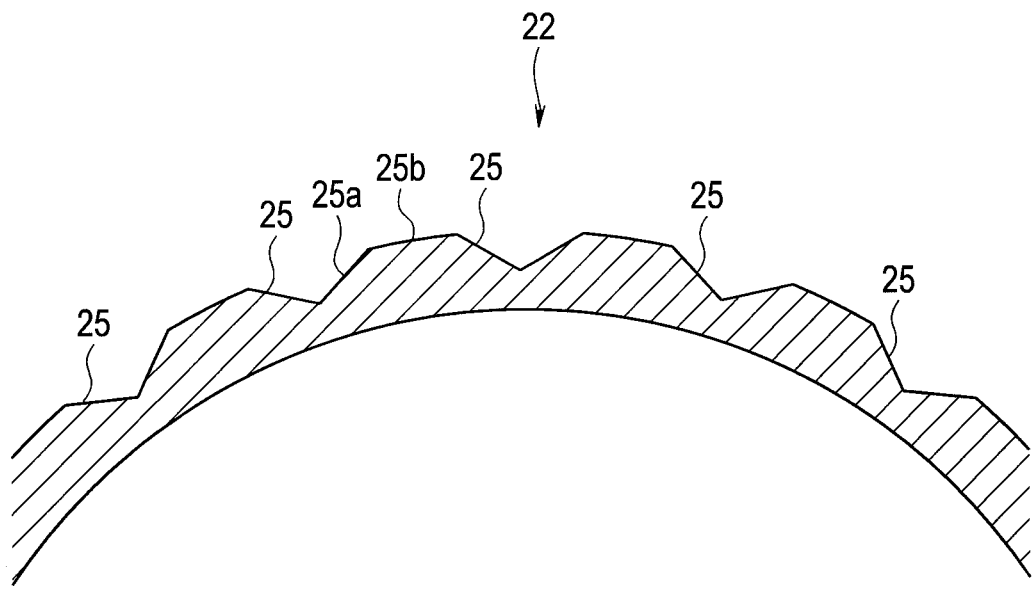
FIG. 13 is a cross-sectional view showing a plurality of V-shaped recesses constituting a grooved portion according to a second modification example.
Figure 14:
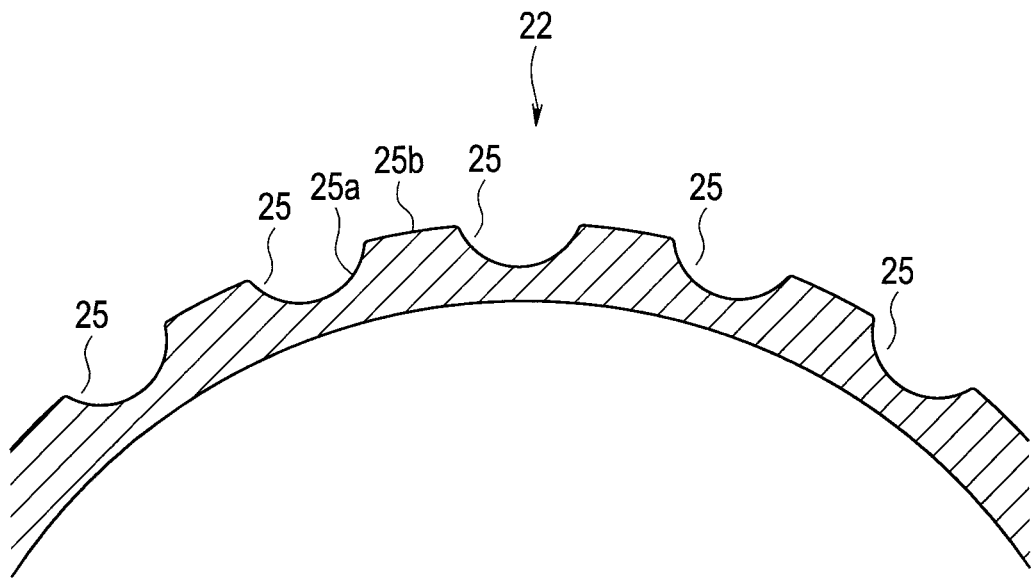
FIG. 14 is a cross-sectional view showing a plurality of arcuate recesses constituting the grooved portion according to the second modification example.
Figure 15:
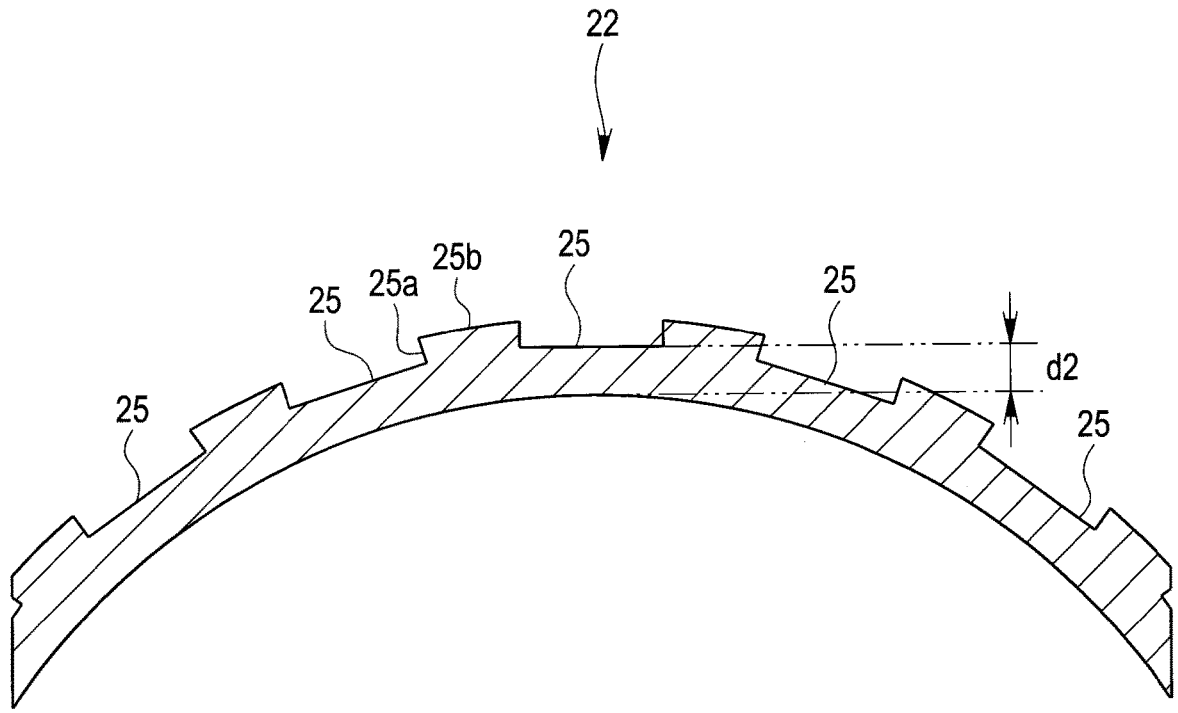
FIG. 15 is a cross-sectional view showing a plurality of rectangular recesses constituting the grooved portion according to the second modification example.
Figure 16:
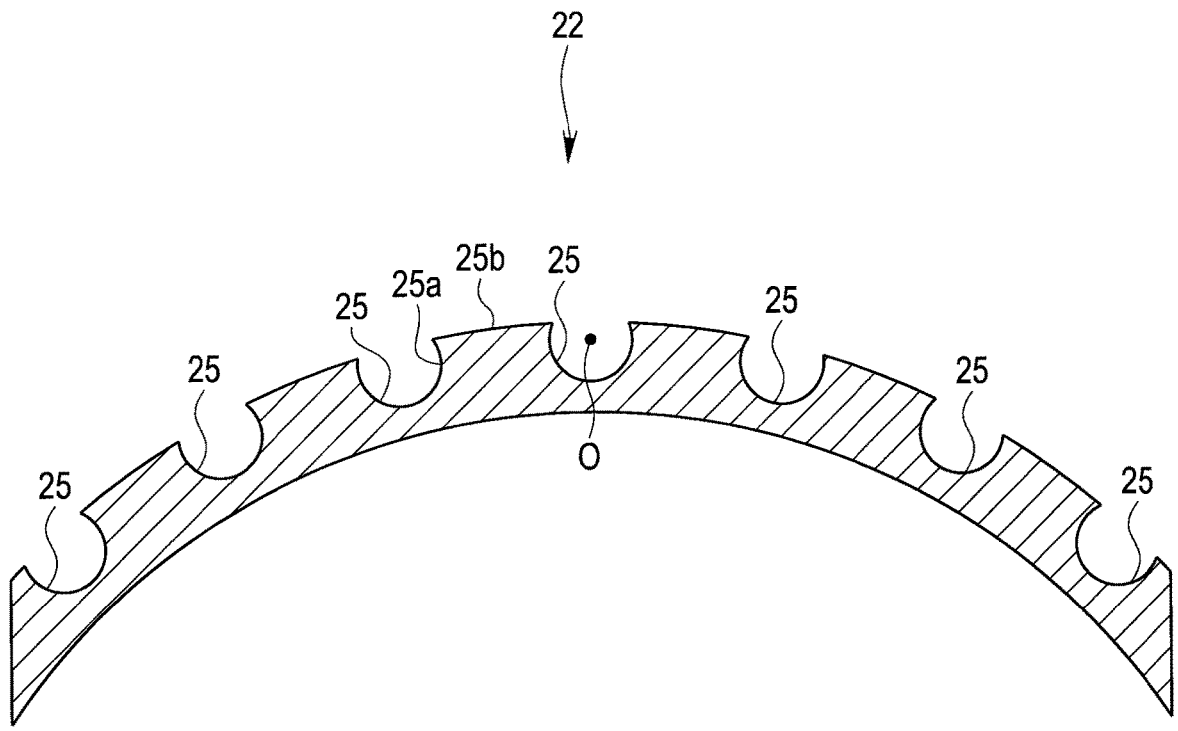
FIG. 16 is a cross-sectional view showing a plurality of arcuate recesses constituting the grooved portion different from FIG. 14 according to the second modification example.

FIG. 13 is a cross-sectional view showing a plurality of V-shaped recesses constituting a grooved portion. FIG. 14 is a cross-sectional view showing a plurality of arcuate recesses constituting the grooved portion. FIG. 15 is a cross-sectional view showing a plurality of rectangular recesses constituting the grooved portion. FIG. 16 is a cross-sectional view showing a plurality of arcuate recesses constituting the grooved portion different from FIG. 14.

As shown in FIG. 13 or 14, the plurality of recesses 25 constituting the grooved portion 26 may be grooves each having a V-shaped cross section or a circular-arc-shaped cross section similarly to those known in the prior art, the angle of a side surface 25a with respect to the outer surface 25b is made to be 90° or less so that the user's fingers are easily caught and then the retaining ring 22 can be easily rotated to be mounted and removed, thereby greatly improving the attachability and detachability of the optical adapter 20.

As shown in FIGS. 15 and 16, as for configuration examples for that, the plurality of recesses 25 constituting the grooved portion 26 may be formed to each have a rectangular cross section, or a circular-arc-shaped cross section whose position of center O is shifted toward the center of the retaining ring 22.

In the case where the plurality of recesses 25 are each rectangular in cross section as shown in FIG. 15, since the angle of the side surface 25a is set to 90° to allow the user's fingers to be easily caught, the depth can be made shallower to make the thickness d2 thicker than before, so that the strength can be further improved.

Furthermore, since the angle of the side surface 25a with the outer surface 25b of the retaining ring 22 being 90° or less is sufficient, the plurality of recesses 25 may have various cross-sectional shapes such as a U-shape, and a shape formed by combining a V-shaped groove and a rectangular groove (similar to a shape of a home-plate used in baseball).

In addition, the grooved portion 26 may be arranged by combining the recesses 25 having the above-described various cross-sectional shapes. Although examples of the grooved portion 26 have been described as a configuration of in which a plurality of groove-shaped recesses 25 extending in the longitudinal direction of the retaining ring 22 are arranged side by side in the circumferential direction of the retaining ring 22, the grooved portion 26 is not limited thereto, and diagonal grooves, or crisscross grooves may also be used.

The invention described in each of the above embodiments is not limited to these embodiments and modification examples, and various modifications can be made in the implementation stage without departing from the gist thereof. Further, each of the above embodiments includes various stages of the invention, and various aspects of the invention can be extracted by appropriately combining a plurality of disclosed constitutional requirements.

For example, in the case where the problem described in the above can be solved and the described effect can be obtained, even if some constituent requirements are deleted from all the constituent requirements shown in each embodiment, a configuration in which the constituent requirements have been deleted can be extracted as the invention.

REFERENCE SIGNS LIST 1 endoscope apparatus
2 apparatus body
3 scope unit
4 LCD
5 operating section
5a grip
5b bending lever
6 universal cable
7 endoscope insertion part
8 tip
9 bending portion
10 flexible tube
11 memory card
14a tip-side first threaded portion
14b tip-side second threaded portion
15 O-ring
20 optical adapter
21 lens holding frame
22 retaining ring
23 objective optical system
24 illumination optical system
25 recess
25a side surface
25b outer surface
26 grooved portion
27 threaded portion (adapter-side second treaded portion)
28 adapter-side first threaded portion
A boundary
d1, d2 wall thickness
L1 to L4 distance
O center

What is claimed is:

1. An endoscope comprising:
a tip having distal and proximal external portions provided on an external surface of the tip; and
an adapter comprising:
a cylindrical body having an internal portion formed on an interior of the cylindrical body, the internal portion being configured to matingly engage with each of the distal and proximal external portions provided on the external surface of the tip of the endoscope, the distal and proximal external portions being separated in a longitudinal direction of the cylindrical body by a portion of the tip that does not engage the internal portion; and
wherein the cylindrical body further having an anti-slip portion formed on an exterior of the cylindrical body, the anti-slip portion having a plurality of recesses arranged circumferentially on the exterior;
the cylindrical body having a first portion with a first wall thickness, a second portion with a second wall thickness greater than the first wall thickness and a boundary between the first portion having the first wall thickness and the second portion having the second wall thickness;
the anti-slip portion is formed on the cylindrical body at the first portion having the first wall thickness; and
a position of the anti-slip portion in the longitudinal direction being set such that:
a position of the proximal external portion in the longitudinal direction does not overlap with the longitudinal position of the anti-slip portion in a state where the proximal external portion is engaged with the internal portion of the cylindrical body, and
a position of the distal external portion in the longitudinal direction is not located at the boundary, in a state where the internal portion is not engaged with the proximal external portion and the cylindrical body is prevented from falling off the tip by the distal external portion.

2. The endoscope according to claim 1, wherein the internal portion is an internal threaded portion and the distal and proximal external portions are distal and proximal threaded portions each being configured to matingly engage with the internal threaded portion.

3. The endoscope according to claim 1, wherein in the state where the proximal external portion is engaged with the internal portion, at least a portion of the distal external portion overlaps with the anti-slip portion in the longitudinal direction.

4. The endoscope according to claim 1, wherein the anti-slip portion being positioned so as to overlap with at least a part of the distal external portion in the longitudinal direction in the state where the proximal external portion is engaged with the internal portion.

5. The endoscope according to claim 1, wherein each of the plurality of recesses having a side surface having an angle of 90° or less with respect to a surface of an outer periphery of a connection ring.

6. The endoscope according to claim 1, further comprising one or more optical elements arranged on the cylindrical body.

7. The endoscope according to claim 1, wherein the second portion having the second wall thickness is superposed on the distal external portion in the longitudinal direction in the state where the internal portion is not engaged with the proximal external portion and the cylindrical body is prevented from falling off the tip by the distal external portion.

8. The endoscope according to claim 1, wherein the second portion having the second wall thickness is superposed in the longitudinal direction on the proximal external portion in the state where the proximal external portion is engaged with the internal portion of the cylindrical body.

* * * * *